(12) United States Patent
Härter et al.

(10) Patent No.: US 7,067,694 B2
(45) Date of Patent: Jun. 27, 2006

(54) HALOGEN-SUBSTITUTED AMINO DICARBOXYLIC ACID DERIVATIVES AS MEDICAMENTS FOR TREATING CARDIOVASCULAR DISEASES

(75) Inventors: Michael Härter, Leverkusen (DE); Michael G. Hahn, Langenfeld (DE); Claudia Hirth-Dietrich, Wuppertal (DE); Andreas Knorr, Erkrath (DE); Elke Stahl, Bergisch Gladbach (DE); Johannes-Peter Stasch, Solingen (DE); Frank Wunder, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 131 days.

(21) Appl. No.: 10/469,180

(22) PCT Filed: Feb. 18, 2002

(86) PCT No.: PCT/EP02/01683
§ 371 (c)(1),
(2), (4) Date: Aug. 26, 2003

(87) PCT Pub. No.: WO02/070460
PCT Pub. Date: Sep. 12, 2002

(65) Prior Publication Data
US 2004/0092593 A1 May 13, 2004

(30) Foreign Application Priority Data
Mar. 1, 2001 (DE) .................... 101 09 858

(51) Int. Cl.
*C07C 63/00* (2006.01)

(52) U.S. Cl. .............. 562/405; 562/433; 562/442; 562/443; 514/579

(58) Field of Classification Search .......... 562/405, 562/433, 442, 443; 514/579
See application file for complete search history.

(56) References Cited

U.S. PATENT DOCUMENTS

| | | | | |
|---|---|---|---|---|
| 6,166,027 A | 12/2000 | Straub et al. | ........ | 514/269 |
| 6,180,656 B1 | 1/2001 | Furstner et al. | ........ | 514/406 |
| 6,387,940 B1 | 5/2002 | Straub et al. | | |
| 6,451,805 B1 | 9/2002 | Straub et al. | ........ | 514/269 |

FOREIGN PATENT DOCUMENTS

| | | |
|---|---|---|
| CA | 2387107 | 3/2001 |
| DE | 19943635 | 3/2001 |
| DE | 19943635 A1 * | 3/2001 |
| EP | 0345068 | 12/1989 |
| WO | 9300359 | 1/1993 |
| WO | 9816223 | 4/1998 |
| WO | 9816507 | 4/1998 |
| WO | 9823619 | 6/1998 |
| WO | 0119355 | 3/2001 |
| WO | 0119776 | 3/2001 |
| WO | 0119778 | 3/2001 |
| WO | 0119780 | 3/2001 |

OTHER PUBLICATIONS

Ko et al., YC–1, a Novel Activator of Platelet Guanylate Cyclase, Blood, 84, 4226–4233 (1994).
Mulsch, et al., Effect of YC–1, an NO–independent, Super-oxide–Sensitive Stimulator of Soluble Gunanylyl Cyclase, on Smooth Muscle Responsiveness to Nitrovasodilators, Brit. J. Pharm. 120, 681–689 (1997).
Glass et al., Stimulation of Human Platelet Guanylate Cyclase by Fatty Acids, J. Biol. Chem., 252, 1279–1285 (1977).
Pettibone et al., A Structurally Novel Stimulator of Guanylate Cyclase with Long–lasting Hypotensive Activity in the Dog, European J. Pharm. 116, 307–312 (1985).
Yu et al., Vasorelaxant Effect of Isoliquiritigenin, a Novel Soluble Guanylate Cyclase Acitvator , in Rat Aorta, Brit. J. Pharm. 114, 1587–1594 (1995).
Gerzer, et al. Soluble Guanylate Cyclase Purified From Bovine Lung Contains Herne and Copper, FEBS letters, 132, 71–74 (1981).
Hoenicka, et al. Purified Soluble Guanylyl Cyclase expressed in Baculovirus/Sf9 system: stimulation by YC–1, nitric oxide, and carbon monoxide J. Mol. Med., 77, 14–23, (1999).
Ignarro, Louis J., Regulation of Cytosolic Guanylyl Cyclase By Porphyrins and Metalloporphyrins, Advances in Pharmacol., 26, 35–65 (1994).
Pinzani, Massino. M.D.; Biology of Hepalc Stellate Cells and Their Possible Relevance in the Pathogenesis of Portal Hypertension in Cirrhosis, Seminars in Liver Disease, 19, 397–410 (1999).

(Continued)

Primary Examiner—Cecilia J. Tsang
Assistant Examiner—Hector M. Reyes

(57) ABSTRACT

Compounds of the general formula (I)

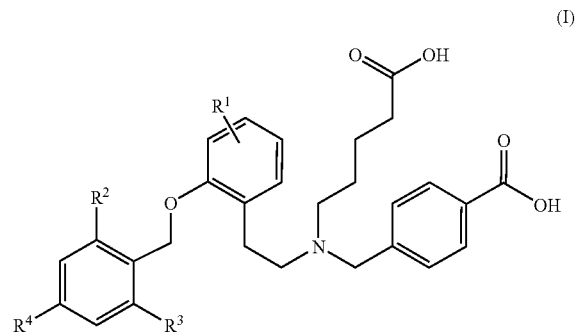

wherein $R^1$ represents halogen, $R^2$ and $R^3$ represent H or halogen, and $R^4$ represents $C_{3-8}$-cycloalkyl or optionally substituted phenyl, pharamceutical compositions containing such materials, and methods of using such materials in the treatment of various diseases are disclosed and claimed.

9 Claims, No Drawings

OTHER PUBLICATIONS

Mülsch, et al., Potentiation of Vascular Responses to NO–Donors by an NO–independent Activation of Soluble Guanylyl Cyclase, Naunyn Schmiedebergs Arch. Pharmacol. 355, R47.

Ko et al., YC–1 a Novel Activator of Platelet Guanylate Cyclase, Blood, 84, 4226–4233 (1994).

Mülsch, et al., Effect of YC–1, an NO–independent, Superoxide–Sensitive Stimulator of Soluble Guanylyl Cyclase, on Smooth Muscle Responsiveness to Nitrovasodilators, Brit. J. Pharm. 120, 681–689 (1997).

Glass et al., Stimulation of Human Platelet Guanylate Cyclase by Fatty Acids, J. Biol. Chem., 252, 1279–1285 (1977).

Pettibone et al., A Structurally Novel Stimulator of Guanylate Cyclase with Long–lasting Hypotensive Activity in the Dog, European J. Pharm. 116, 307–312 (1985).

Yu et al., Vasorelaxant Effect of Isoliquiritigenin, a Novel Soluble Guanylate Cyclase Activator, in Rat Aorta, Brit. J. Pharm. 114, 1587–1594 (1995).

Gerzer, et al. Soluble Guanylate Cyclase Purified From Bovine Lung Contains Heme and Copper, FEBS letters, 132, 71–74, (1981).

Hoenicka, et al. Purified Soluble Guanylyl Cyclase expressed in Baculovirus/Sf9 system: stimulation by YC–1, nitric oxide, and carbon monoxide J. Mol. Med., 77, 14–23, (1999).

Ignarro, Louis J., Regulation of Cytosolic Guanylyl Cyclase By Porphyrins and Mettaloporphyrins, Advances in Pharmacol., 26, 35–65 (1994).

Pinzani, et al; Biology of Hepatic Stellate Cells and Their Possible Relevance in the Pathogenesis of Portal Hypertension in Cirrhosis, Seminars in Liver Disease, 19, 397–410, (1999).

Mülsch, et al., Potentiation of Vascular Responses to NO–Donors by and NO–independent Activation of Soluble Guanylyl Cyclase, Naynym Schmiedebergs Arch. Pharmacol. 355, R47.

* cited by examiner

HALOGEN-SUBSTITUTED AMINO DICARBOXYLIC ACID DERIVATIVES AS MEDICAMENTS FOR TREATING CARDIOVASCULAR DISEASES

The present invention relates to novel halogen-substituted aminocarboxylic acid derivatives which stimulate soluble guanylate cyclase also via a novel mechanism of action which takes place without involvement of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory center. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in the neuronal signal transmission, and in disorders caused by an impairment of the aforementioned processes. Under pathophysiological conditions, the NO/cGMP system may be suppressed, which may lead for example to high blood pressure, platelet activation, increased cell proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmcol. 116 (1985), 307), isoliquiritigenin (Yu et al., Brit. J. Pharmacol. 114 (1995), 1587) and various substituted pyrazole derivatives (WO 98/16223, WO 98/16507 and WO 98/23619).

The stimulators of soluble guanylate cyclase described above stimulate the enzyme either directly via the heme group (carbon monoxide, nitrogen monoxide or diphenyliodonium hexafluorophosphate) by interaction with the central iron of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating action of NO or CO (for example YC-1, Hoenicka et al., J. Mol. Med. (1999) 14; or the pyrazole derivatives described in WO 98/16223, WO 98/16507 and WO 98/23619).

The stimulating action of isoliquiritigenin and of fatty acids, such as, for example, arachidonic acid, prostaglandin endoperoxides and fatty acid hydroperoxides, on soluble guanylate cyclase claimed in the literature could not be confirmed (cf., for example, Hoenicka et al., J. Mol. Med. 77 (1999), 14).

If the heme group is removed from soluble guanylate cyclase, the enzyme still has detectable catalytic basal activity, i.e. cGMP is still being formed. The residual catalytic basal activity of the heme-free enzyme cannot be stimulated by any of the known stimulators mentioned above.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, as a consquence of which the addition of protoporphyrin IX to soluble guanylate cyclase would be expected to result in the formation of a structure of the enzyme corresponding to heme-containing soluble guanylate cyclase stimulated by NO. This is also confirmed by the fact that the stimulating action of protoporphyrin IX is increased by the above-described NO-independent but heme-dependent stimulator YC-1 (Mülsch et al., Naunyn Schmiedebergs Arch. Pharmacol. 355, R47).

In contrast to the above-described compounds, known from the prior art as stimulators of soluble guanylate cyclase, the compounds according to the invention are capable of stimulating both the heme-containing and the heme-free form of soluble guanylate cyclase. Thus, in the case of these novel stimulators, stimulation of the enzyme is effected via a heme-independent path, and this is also confirmed by the fact that firstly the novel stimulators do not have any synergistic action with NO at the heme-containing enzyme and that secondly the action of these novel stimulators cannot be blocked by the heme-dependent inhibitor of soluble guanylate cyclase, i.e. 1H-1,2,4-oxadiazole-(4,3a)-quinoxalin-1-one (ODQ).

This is a novel therapeutic approach for treating cardiovascular disorders and other disorders accessible to therapy by influencing the cGMP signal pathway in organisms.

EP-A-0 345 068 describes, inter alia, the aminoalkanecarboxylic acid (1) as an intermediate in the synthesis of GABA antagonists:

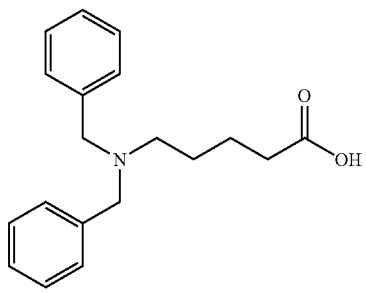

(1)

WO 93/00359 describes the aminoalkanecarboxylic acid (2) as an intermediate in peptide synthesis and its use as active compound for treating disorders of the central nervous system:

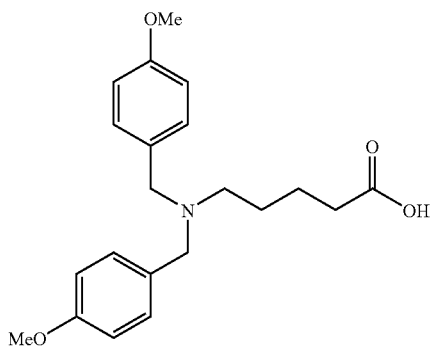

(2)

However, neither of these two publications describes that such aminoalkanecarboxylic acids may have a stimulating effect, independent of the heme group present in the enzyme, on soluble guanylate cyclase.

Substances having a structure similar to that of the compounds according to the invention are furthermore known from WO 01/19776, WO 01/19355, WO 01/19780 and WO 01/19778.

The present invention relates to compounds of the general formula (I)

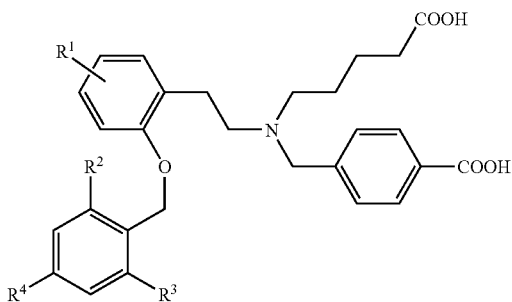

(I)

where
$R^1$ is located in the meta- or para-position to the ethylamino radical and represents halogen;
$R^2$ represents H or halogen;
$R^3$ represents H or halogen;
$R^4$ represents $C_{3-8}$-cycloalkyl or phenyl, where the phenyl radical may additionally carry a substituent from the group consisting of halogen, CN, OMe, $CF_3$;

with the proviso that $R^4$ may not represent phenyl which carries a substituent $CF_3$ or OMe in the para-position to the point of attachment if, simultaneously, $R^1$ is in the meta-position to the ethylamino radical and represents F and $R^2$ and $R^3$ each represent H;
and their salts, isomers and hydrates.

According to a preferred embodiment, the present invention relates to compounds of the formula (I) where
$R^1$ is located in the meta- or para-position to the ethylamino radical and represents F, Cl or Br;
$R^2$ represents H or F or Cl;
$R^3$ represents H;
$R^4$ represents cyclohexyl or phenyl, where the phenyl radical may additionally carry a substituent from the group consisting of F, Cl, Br, CN, OMe, $CF_3$;
with the proviso that $R^4$ may not represent phenyl which carries a substituent $CF_3$ or OMe in the para-position to the point of attachment if, simultaneously, $R^1$ is in the meta-position to the ethylamino radical and represents F and $R^2$ and $R^3$ each represent H;
and their salts, isomers and hydrates.

According to a particularly preferred embodiment, the present invention relates to compounds of the formula (I) where
$R^1$ is located in the meta-position to the ethylamino radical and represents Cl;
$R^2$ represents H or Cl;
$R^3$ represents H;
$R^4$ represents cyclohexyl or phenyl, where the phenyl radical may additionally carry a substituent from the group consisting of F, Cl, CN, OMe, $CF_3$;
and their salts, isomers and hydrates.

According to a further particularly preferred embodiment, the present invention relates to compounds of the formula (I) in which
$R^1$ is located in the para-position to the ethylamino radical and represents Cl or F;
$R^2$ represents H or Cl;
$R^3$ represents H;
$R^4$ represents cyclohexyl or phenyl, where the phenyl radical may additionally carry a substituent from the group consisting of F, Cl, CN, OMe, $CF_3$;
and their salts, isomers and hydrates.

The compounds according to the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers), or not like image and mirror image (diastereomers). The invention relates both to the enantiomers or diastereomers and to their respective mixtures. The racemic forms, like the diastereomers, can be separated into the stereoisomerically uniform components in a known manner, for example by optical resolution or chromatographic separation. Double bonds present in the compounds according to the invention can be in the cis or trans configuration (Z or E form).

For the purposes of the present invention, the substituents are, unless defined otherwise, generally as defined below:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Cycloalkyl generally represents a cyclic hydrocarbon radical having 3 to 8 carbon atoms. Preference is given to cyclopropyl, cyclopentyl and cyclohexyl. Cyclopentyl, cyclohexyl, cycloheptyl and cyclooctyl may be mentioned by way of example.

Halogen, for the purposes of the invention, represents fluorine, chlorine, bromine and iodine.

The present invention furthermore relates to a process for preparing the compounds of the formula (I), characterized in that compounds of the formula (II)

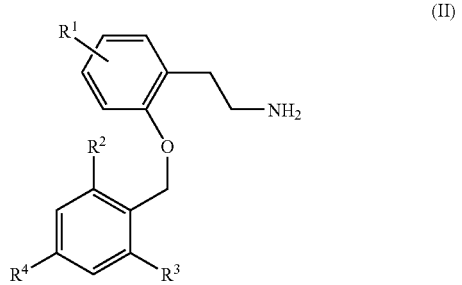

in which $R^1$, $R^2$, $R^3$ and $R^4$ are as defined above, are reacted with a $C_{1-6}$-alkyl 4-formylbenzoate in an organic solvent with heating and with simultaneous or subsequent addition of a reducing agent to give compounds of the formula (III)

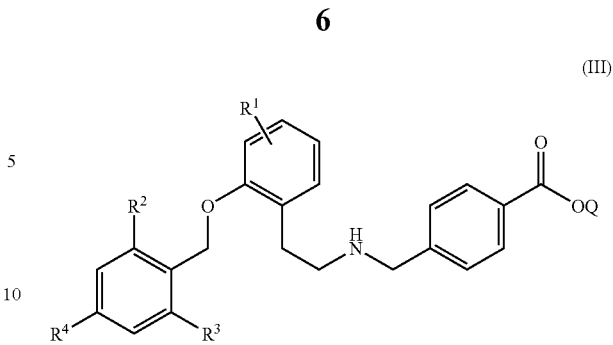

where
$R^1$, $R^2$, $R^3$ and $R^4$ are as defined above and Q represents a $C_{1-6}$-alkyl radical,
then reacted with a $C_{1-6}$-alkyl ω-halovalerate in an organic solvent in the presence of a base with heating to give compounds of the formula (IV)

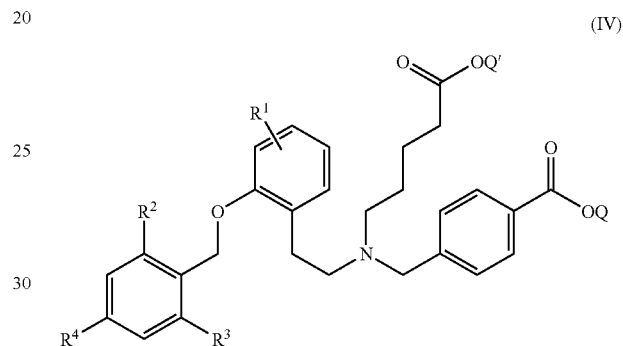

where
$R^1$, $R^2$, $R^3$ and $R^4$ and Q are as defined above and Q' represents a $C_{1-6}$-alkyl radical,
and the compounds of the formula (IV) are then hydrolyzed under alkaline conditions to give the compounds of the formula (I).

Bases which are preferred for the processes according to the invention include basic compounds which are customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t-butoxide, or carbonates, such as sodium carbonate, cesium carbonate or potassium carbonate, or amides, such as sodium amide or lithium diisopropylamide, or organolithium compounds, such as phenyllithium, butyllithium or methyllithium, or sodium hexamethyldisilazane.

Solvents which are preferred for converting the compounds of the formula (II) into the compounds of the formula (III) are customary organic solvents which do not change under the reaction conditions. Preference is given to using, for the process according to the invention, ethers, such as diethyl ether, butyl methyl ether, dioxane, tetrahydrofuran, glycol dimethyl ether or diethylene glycol dimethyl ether, or hydrocarbons, such as benzene, toluene, xylene or petroleum ether, or alcohols, such as methanol or ethanol, or halogenated hydrocarbons, such as carbon tetrachloride, chloromethane or dichloromethane. It is, of course, also possible to use mixtures of the solvents mentioned above. Preference according to the invention is given to using toluene and/or methanol.

The compounds of the formula (II) are reacted initially with a $C_{1-6}$-alkyl 4-formylbenzoate giving a Schiff base which is then reduced with customary reducing agents, such as, for example, NaBH$_4$, H$_2$/Pd/C, etc., or reacted directly under the conditions of a reductive alkylation in the presence of a reducing agent, such as, for example, H$_2$/Pd/C, NaCNBH$_3$, NaH(OAc)$_3$ (cf. Patai, Ed., The Chemistry of the Carbon-Nitrogen Double Bond, pp. 276–293 and the literature cited therein). Depending on the nature of the starting material, the reaction can be carried out at room temperature or requires heating at 50–110° C. for a number of hours to a number of days. The reaction can be carried out at atmospheric pressure, elevated or reduced pressure (for example in a range of from 0.5 to 5 bar). In general, the reaction is carried out at atmospheric pressure. C$_{1-6}$-Alkyl 4-formylbenzoates are commercially available, known from the literature, or they can be synthesized analogously to processes known from the literature (cf., for example, J. Med. Chem. 1989, 32, 1277; Chem. Ber. 1938, 71, 335; Bull. Soc. Chim. Fr. 1996, 123, 679; WO96/11902; DE-2209128; Synthesis 1995, 1135; Bull. Chem. Soc. Jpn. 1985, 58, 2192, Synthesis 1983, 942; J. Am. Chem. Soc. 1992, 114, 8158).

The conversion of the compounds of the formula (III) into the compounds of the formula (IV) can preferably be carried out in acetonitrile or butyronitrile, in each case in the presence of a base, such as sodium carbonate, Et$_3$N, DABCO, K$_2$CO$_3$, KOH, NaOH or NaH. In general, the reaction can be carried out in a temperature range of from −20° C. to +90° C., preferably from 0° C. to +70° C. The reaction can be carried out under atmospheric pressure, elevated or reduced pressure (for example in a range of from 0.5 to 5 bar). In general, the reaction is carried out under atmospheric pressure. However, suitable solvents are, in principle, the solvents mentioned above for the conversion of the compounds of the formula (II) into the compounds of the formula (II). According to the invention, the alkyl ω-halovalerate used is, preferably, the corresponding methyl 1-bromovalerate. Alkyl ω-halovalerates are commercially available, known from the literature or can be synthesized according to processes known from the literature (cf., for example, J. Chem. Soc. 1958, 3065).

The compounds of the formula (IV) are then converted into the compounds of the formula (I) by hydrolysis of the ester functions to the free carboxyl groups, for example by adding aqueous solutions of strong acids, such as, for example, HCl or H$_2$SO$_4$, or strong bases, such as, for example, NaOH, KOH or LiOH. The reaction can be carried out in one of the organic solvents mentioned above, in water or in mixtures of organic solvents or in mixtures of organic solvents with water. Preference according to the invention is given, for example, to carrying out the reaction in a mixture of water and methanol or dioxane. In general, the reaction can be carried out in a temperature range of from −20° C. to +90° C., preferably from 0° C. to +90° C. The reaction can be carried out under atmospheric pressure, elevated or reduced pressure (for example in a range of from 0.5 to 5 bar). In general, the reaction is carried out under atmospheric pressure.

If the compounds of the formula (II) are not commercially available, they can be obtained in the manner described below. 4- or 5-halo-2-hydroxybenzaldehydes, which are commercially available or known from the literature, give, by reaction with appropriate benzyl halides, preferably benzyl chlorides, substituted in the 4-position in an organic solvent, such as acetonitrile, in the presence of a base, such as, for example, potassium carbonate, reaction of the aldehyde group with nitromethane in an organic solvent, such as, for example, ethanol, in the presence of a base, such as, for example, methylamine, and reduction of the resulting nitroethenyl function in two steps, initially with an alkali metal hydride, such as, for example, LiAl$_4$, to give the corresponding hydroxylamine ethyl function, and then with Zn in acidic medium, such as, for example, in the presence of acetic acid, the corresponding amine of the formula (II).

The compounds of the general formula (I) according to the invention show a valuable range of pharmacological effects which could not have been predicted.

The compounds of the general formula (I) according to the invention bring about vasorelaxation and an inhibition of platelet aggregation and lead to a reduction in blood pressure and an increase in the coronary blood flow. These effects are mediated by direct stimulation of soluble guanylate cyclase and an intracellular increase in cGMP.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenosis such as after thrombolysis therapies, percutaneous transluminal angioplasties (PTAs), percutaneous transluminal coronary angioplasties (PTCAs), bypass and for the treatment of arteriosclerosis, fibrotic disorders, such as fibrosis of the liver or pulmonary fibrosis, asthmatic disorders and diseases of the urogenital system such as, for example, prostate hypertrophy, erectile dysfunction, female sexual dysfunction and incontinence and also for the treatment of glaucoma.

The compounds of the general formula (I) described in the present invention are also active compounds suitable for controlling central nervous system diseases characterized by disturbances of the NO/cGMP system. They are suitable in particular for removing cognitive deficits, for improving learning and memory performances and for treating Alzheimer's disease. They are also suitable for treating disorders of the central nervous system such as states of anxiety, tension and depression, CNS-related sexual dysfunctions and sleep disturbances, and for controlling pathological disturbances of the intake of food, stimulants and addictive substances.

The active compounds are furthermore also suitable for regulating cerebral blood flow and thus represent effective agents for controlling migraine.

They are also suitable for the prophylaxis and control of the sequelae of cerebral infarction (apoplexia cerebri) such as stroke, cerebral ischemias and craniocerebral trauma. The compounds of the general formula (I) according to the invention can likewise be employed for controlling states of pain.

In addition, the compounds according to the invention have an anti-inflammatory effect and can therefore be employed as anti-inflammatory agents.

As a particular and surprising feature, the compounds of the present invention have an unexpectedly long duration of action.

Vasorelaxant Effect in vitro

Rabbits are anesthetized or killed by intravenous injection of thiopental sodium (about 50 mg/kg) and exsanguinated. The arteria saphena is removed and divided into rings 3 mm wide. The individual rings are in each case mounted on a pair of hooks of triangular shape, open at the ends and made of special wire (Remanium®) having a diameter of 0.3 mm. Under pretension, each ring is introduced into a 5 ml organ bath containing carbogen-gassed Krebs-Henseleit solution at 37° C. with the following composition (mM): NaCl: 0.119; KCl: 4.8; CaCl$_2$×2H$_2$O: 1; MgSO$_4$×7H$_2$O: 1.4; KH$_2$PO$_4$: 1.2; NaHCO$_3$: 25; glucose: 10; bovine serum albumin: 0.001%. The force of contraction is detected with Statham UC2 cells, amplified and digitized via A/D converters (DAS-1802 HC, Keithley Instruments, Munich) and recorded in parallel on chart recorders. Contractions are generated by adding phenylephrine.

After several (generally 4) control cycles, the substance to be investigated is added in each further run in increasing dosage, and the height of the contraction reached under the influence of the test substance is compared with the height of the contraction reached in the last preceding run. The concentration necessary to reduce the height of the control value by 50% ($IC_{50}$) is calculated from this. The standard application volume is 5 µl. The DMSO content in the bath solution corresponds to 0.1%.

The results are shown in Table 1:
Table 1: Vasorelaxant effect in vitro

TABLE 1

| Vasorelaxant effect in vitro | |
|---|---|
| Example | $IC_{50}$ (nM) |
| 1 | 1.1 |
| 2 | 1.5 |
| 3 | 1 |
| 6 | 8.1 |
| 9 | 8.3 |

Stimulation of Recombinant Soluble Guanylate Cyclase (sGC) in vitro

The investigations of the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out according to the method described in detail in the following literature reference: M. Hoenicka, E. M. Becker, H. Apeler, T. Sirichoke, H. Schroeder, R. Gerzer and J.-P. Stasch: Purified soluble guanylyl cyclase expressed in a baculovirus/Sf9 system: stimulation by YC-1, nitric oxide, and carbon oxide. J. Mol. Med. 77 (1999): 14–23.

The heme-free guanylate cyclase was obtained by adding Tween 20 to the sample buffer (final concentration 0.5%).

Activation of sGC by a test substance is stated as n-fold stimulation of basal activity.

Investigation of the Antifibrotic Action of the Substances in vivo

Method

The antifibrotic action of the substances was investigated using the model of the porcine serum-induced rat liver fibrosis. Treatment with heterologous serum, for example porcine serum in rats, is a method frequently used in the literature for inducing fibrosis of the liver with subsequent cirrhosis which, in contrast to other models, causes only minimal damage and inflammation of the parenchyma cells of the liver (Bhunchet, E. and Wake, K. (1992): Role of mesenchymal cell populations in porcine serum-induced rat liver fibrosis. Hepatology 16: 1452–1473). Female Sprague Dawley rats were treated 2× per week with 0.5 ml/animal of sterile porcine serum (Sigma) i.p., control animals were treated with sterile physiological saline (2× per week 0.5 ml/animal i.p.). The treatment with test substance (1× per day in 5 ml/kg of p.o. solvent comprising 20% Cremophor, 10% Transcutol and 70% $H_2O$) was carried out in parallel to the treatment with porcine serum. After seven weeks of treatment, the animals were killed and the livers were removed in order to quantify the collagen content.

For the histological examination of the liver tissue, standardized transverse tissue cylinders (about 10×2 mm) were punched out of the right anterior lobe of the liver.

For the detection of scar collagen caused by liver fibrosis, frozen sections were stained with 0.1% strength Pikrosirius Red solution.

Fast Green was used as counterstain to enhance contrasts. In each section, the extent of liver fibrosis was determined as a percentage of the area stained by Pikrosirius Red of the total area measured. The parameters of the video microscopic stain detection were standardized and kept constant for the entire experiment. 64 fields of a standardized grid of 31 $mm^2$ were measured using a final amplification of 100. For semiautomatic morphometry, a Leica Quantimed 500MC (Leica Germany) was used.

To determine OH-proline according to Prockop and Udenfried (Prockop, D. J. and Udenfried, S. A. (1960): A specific method for the analysis of hydroxyproline in tissues and urine. Anal. Biochem. 1: 228–239), in each case 50–100 mg of liver tissue were dried and boiled with 6N HCl for about 17 hours. The acid was evaporated in a vacuum drying cabinet and the residue was then dissolved in 5 ml of distilled water and filtered. 200 µl of the filtered solution were incubated at room temperature with 200 µl of ethanol and 200 µl of oxidation solution (7% strength aqueous chloramine T hydrate solution, diluted 1:4 with acetate/citrate buffer pH 6.0) for 25 min. 400 µl of Ehrlich's reagent (12 g of 4-dimethylaminobenzaldehyde in 20 ml of ethanol+2.74 ml of concentrated sulfuric acid in 20 ml of ethanol) were then added. After 3 hours of incubation at 35° C., absorption at 573 nm was measured. Aqueous OH-proline solutions (Sigma) were used for the calibration curve. The OH-proline content of the liver samples was calculated in mg per g of liver dry weight.

Results

The OH-proline values agree very well with the results of the morphometric fibrosis measurement: without simultaneous administration of substance, the porcine serum treatment results in a pronounced accumulation of collagen in the liver. The formation of these collagen deposits is reduced by treatment with the substances in a dose-dependent manner.

The present invention includes pharmaceutical preparations which, in addition to non-toxic, inert, pharmaceutically acceptable carriers, comprises the compounds according to the invention, in particular the compounds of the general formula (I), and processes for preparing these preparations.

The active compound, if appropriate in one or more of the carriers listed above, can also be present in microencapsulated form.

The therapeutically effective compounds, in particular the compounds of the general formula (I), should be present in the pharmaceutical preparations detailed above in a concentration of about 0.1 to 99.5, preferably of about 0.5 to 95, % by weight of the complete mixture.

The pharmaceutical preparations detailed above may, apart from the compounds according to the invention, in particular the compounds of the general formula (I), also contain other active pharmaceutical ingredients.

It has generally proved to be advantageous both in human and in veterinary medicine to administer the active compound(s) according to the invention in total amounts of about 0.5 to about 500, preferably 5 to 100, mg/kg of body weight every 24 hours, where appropriate in the form of a plurality of single doses, to achieve the desired results. A single dose contains the active compound(s) according to the invention preferably in amounts of about 1 to about 80, in particular 3 to 30, mg/kg of body weight.

Below, the present invention is illustrated in more detail using non-limiting preferred examples. Unless indicated otherwise, all quantities refer to percent by weight.

EXAMPLES

Abbreviations:

| | |
|---|---|
| RT: | room temperature |
| EA: | ethyl acetate |
| BABA: | n-butyl acetate/n-butanol/glacial acetic acid/phosphate buffer pH 6 (50:9:25.15; org. phase) |

Mobile Phases for Thin-layer Chromatography:

| T1 E1: | toluene-ethyl acetate (1:1) |
|---|---|
| T1 EtOH1: | toluene-methanol (1:1) |
| C1 E1: | cyclohexane-ethyl acetate (1:1) |
| C1 E2: | cyclohexane-ethyl acetate (1:2) |

Starting Materials

Ex. I

2-[(4-cyclohexylbenzyl)oxy]-4-fluorobenzaldehyde

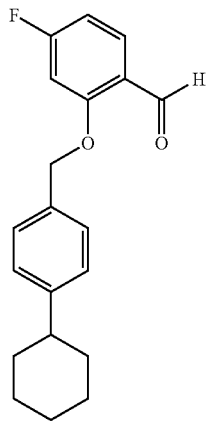

2 g (14.3 mmol) of 2-hydroxy-4-fluorobenzaldehyde (CAS 348-28-7) and 2.37 g (17.1 mmol) of anhydrous potassium carbonate are added to a solution of 3.13 g (15 mmol) of 4-cyclohexylbenzyl chloride (CAS 4463-31-4) in 50 ml of dry acetonitrile, and the mixture is heated at reflux for six hours. The mixture is then concentrated to dryness using a rotary evaporator, water and a little ether are added and the insoluble product is isolated by filtration. This gives 4.4 g (14.1 mmol, 99% yield) of a solid.

$R_f$ (cyclohexane/ethyl acetate 1:1): 0.77. $^1$H NMR (300 MHz, DMSO-$d_6$, δ/ppm): 10.29 (1H, s), 7.78 (1H, dd), 7.41 (2H, d), 7.28–7.20 (3H, m), 6.93 (1H, dt), 5.26 (2H, s), 2.50 (1H, m, partially obscured by DMSO), 1.83–1.67 (5H, m), 1.47–1.18 (5H, m). MS (DCI, NH$_3$): 642 (2M+NH$_4^+$), 502, 330 (M+NH$_4^+$), 207.

Ex. II

2-[(4-cyclohexylbenzyl)oxy]-4-fluoro-1-[2-nitroethenyl]benzene

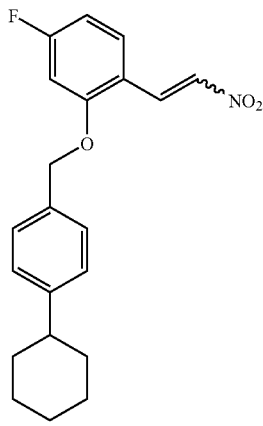

A mixture of 460 mg of anhydrous sodium carbonate and 460 mg of methylamine hydrochloride in 5 ml of absolute ethanol is stirred for 15 minutes and then filtered into a solution of 4.4 g (14.09 mmol) of 2-[(4-cyclohexylbenzyl)oxy]4-fluorobenzaldehyde from Ex. I. 1.18 ml (21.69 mmol) of nitromethane and a spatula tip of sodium acetate are added. The mixture is heated at 60° C. After a while, a yellow solid begins to precipitate. After three hours, the reaction is ended. The mixture is cooled in an ice/water bath and the precipitated product is then filtered off and washed with a little cold ethanol. This gives 3.65 g (10.27 mmol, 73% yield) of a yellow solid.

Melting point: 86° C. $R_f$ (cyclohexane/dichloromethane 4:1): 0.64. $^1$H-NMR (400 MHz, DMSO-$d_6$, δ/ppm): 8.18 (1H, d), 8.07 (1H, d), 7.92 (1H, dd), 7.41 (2H, d), 7.29 (2H, d), 7.23 (1H, dd), 6.94 (1H, dt), 5.27 (2H, s), 2.52 (1H, m, partially obscured by DMSO), 1.81–1.67 (5H, m), 1.47–1.19 (5H, m). MS (DCI, NH$_3$): 390 (M+NH$_3$+NH$_4^+$), 373 (M+NH$_4^+$).

Ex. III

2-{2-[(4-cyclohexylbenzyl)oxy]-4-fluorophenyl}ethylamine

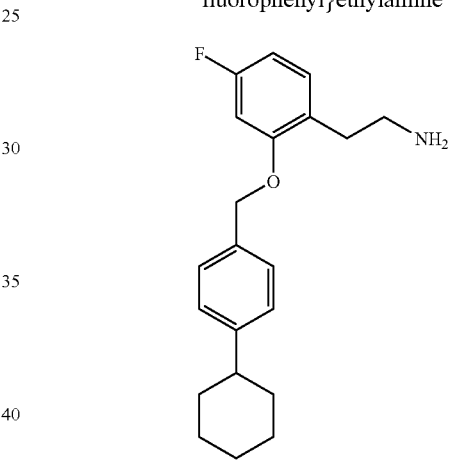

30.5 ml (30.5 mmol) of a 1-molar solution of LiAlH$_4$ in THF is diluted with a further 20 ml of anhydrous THF, and, at −78° C., a solution of 3.6 g (10.13 mmol) of 2-[(4-cyclohexylbenzyl)oxy]-4-fluoro-1-[2-nitroethenyl]benzene from Ex. II in 30 ml of anhydrous THF is added dropwise. The mixture is stirred initially at −78° C. for 30 minutes and then at 0° C. for 30 minutes. 50 ml of aqueous sodium potassium tartrate solution are then added carefully, the mixtureis diluted with ether and the organic phase is separated off. The organic phase is washed successively with water and saturated sodium chloride solution, dried over anhydrous sodium sulfate and, after filtration, freed from the solvent. The resulting crude product is purified by flash chromatography (silica gel, cyclohexane/ethyl acetate 1:1). This gives 1.25 g (3.64 mmol, 38% yield) of N-(2-{2-[(4-chlorohexylbenzyl)oxy]-4-fluorophenyl}ethyl) hydroxylamine.

$R_f$ (cyclohexane/ethyl acetate 1:1): 0.10. $^1$H-NMR (200 MHz, DMSO-$d_6$, δ/ppm): 7.38 (2H, d), 7.27–7.12 (4H, m), 6.92 (1H, dd), 6.68 (1H, dt), 5.61 (1H, s broad), 5.07 (2H, s), 2.93–2.85 (2H, m), 2.78–2.68 (2H, m), 2.49 (1H, m, partially obscured by DMSO), 1.84–1.66 (5H, m), 1.49–1.27 (5H, m). MS (DCI, NH$_3$): 344 (M+H$^+$).

1.05 g (3.06 mmol) of N-(2-{2-[(4-cyclohexylbenzyl)oxy]-4-fluorophenyl}ethyl)-hydroxylamine are dissolved in 10 ml of glacial acetic acid, and 1 g (15.29 mmol) of zinc dust is added a little at a time. After 20 hours of stirring at room temperature, the mixture is stirred into an excess of saturated sodium bicarbonate solution. The mixture is extracted with ethyl acetate. The combined extracts are washed successively with saturated sodium bicarbonate solution, water and saturated sodium chloride solution. Drying over sodium sulfate. This gives 1.0 g (3.05 mmol, 99% yield) of product.

$R_f$ (ethyl acetate/methanol 7:3): 0.08. $^1$H-NMR (400 MHz, DMSO-$d_6$, δ/ppm): 7.37 (2H, d), 7.23 (2H, d), 7.14 (1H, dd), 6.92 (1H, dd), 6.68 (1H, dt), 5.06 (2H, s), 2.73–2.70 (2H, m), 2.67–2.62 (2H, m), 2.49 (1H, m, partially obscured by DMSO), 1.90 (2H, s broad), 1.80–1.68 (5H, m), 1.42–1.20 (5H, m). MS (DCI, $NH_3$): 328 (M+H$^+$).

Ex. IV

Methyl 4-{[(2-{2-[(4-cyclohexylbenzyl)oxy]-4-fluorophenyl}ethyl)-amino]methyl}benzoate

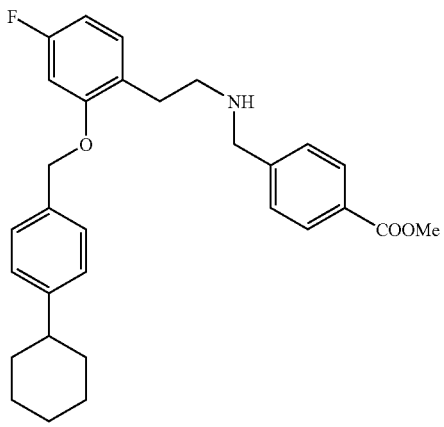

500 mg (1.53 mmol) of 2-{2-[(4-cyclohexylbenzyl)oxy] 4-fluorophenyl}ethylamine from Ex. III and 251 mg (1.53 mmol) of methyl 4-formylbenzoate in 50 ml of toluene are boiled in a water separator for 30 minutes. The toluene is then removed using a rotary evaporator and replaced by 15 ml of methanol. At 0° C., 58 mg (1.53 mmol) of NaBH$_4$ are added to the methanolic solution and the mixture is then stirred at room temperature for 30 minutes. The mixture is neutralized by addition of 5% strength aqueous sodium dihydrogen phosphate solution and diluted with ether and water, and the organic phase is separated off. After drying over Na$_2$SO$_4$ and evaporation of the solvent, the product is purified by flash chromatography (silica gel, cyclohexane/ethyl acetate 1:1). This gives 436 mg (0.92 mmol, 60% yield) of a colorless oil.

$R_f$ (cyclohexane/ethyl acetate 1:1): 0.17. $^1$H-NMR (300 MHz, DMSO-$d_6$, δ/ppm): 7.87 (2H, d), 7.41 (2H, d), 7.29 (2H, d), 7.19 (2H, d), 7.14 (1H, dd), 6.90 (1H, dd), 6.67 (1H, dt), 5.02 (2H, s), 3.83 (3H, s), 3.76 (2H, s), 2.73–2.62 (4H, m), 2.48 (1H, m, partially obscured by DMSO), 2.40 (1H, broad), 1.81–1.68 (5H, m), 1.43–1.20 (5H, m). MS (ESI): 476 (M+H$^+$).

Ex. V

Methyl 4-{[(2-{2-[(4-cyclohexylbenzyl)oxy]-4-fluorophenyl}ethyl)(5-methoxy-5-oxo-pentyl)amino]methyl}benzoate

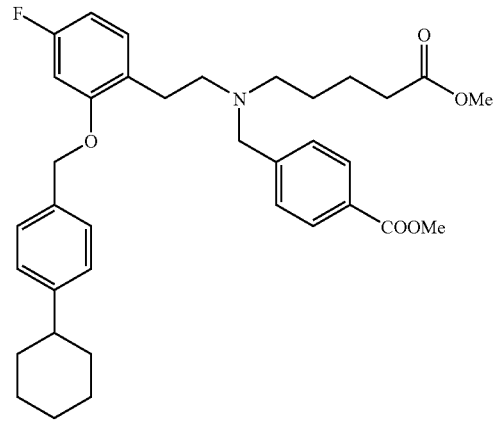

54 mg (0.50 mmol) of anhydrous sodium carbonate are added to a solution of 200 mg (0.42 mmol) of methyl 4-{[(2-{2-[(4-cyclohexylbenzyl)oxy]-4-fluorophenyl}ethyl)amino]methyl}benzoate from Ex. IV and 67 µl (0.50 mmol) of methyl 5-bromovalerate in 10 ml of butyronitrile, and the mixture is heated at reflux for 48 hours. The mixture is then concentrated, taken up in ethyl acetate and washed with water. After drying over Na$_2$SO$_4$, filtration and concentration, the product is purified by flash chromatography (silica gel, cyclohexane/ethyl acetate 9:1). This gives 150 mg (0.25 mmol, 60% yield) of a colorless oil.

$R_f$ (cyclohexane/ethyl acetate 1:1): 0.66. $^1$H-NMR (300 MHz, DMSO-$d_6$, δ/ppm): 7.83 (2H, d), 7.33 (2H, d), 7.27 (2H, d), 7.18 (2H, d), 7.12 (1H, dd), 6.90 (1H, dd), 6.66 (1H, dt), 4.97 (2H, s), 3.83 (3H, s), 3.59 (2H, s), 3.54 (3H, s), 2.72–2.65 (2H, m), 2.58–2.51 (2H, m), 2.48 (1H, m, partially obscured by DMSO), 2.39 (2H, t), 2.17 (2H, t), 1.80–1.67 (5H, m), 1.46–1.23 (9H, m). MS (ESI): 590 (M+H$^+$).

Synthesis Examples

Ex. 1

4-{[(4-carboxybutyl)(2-{2-[(4-cyclohexylbenzyl)oxy]-4-fluorophenyl}ethyl)amino]methyl}benzoic acid

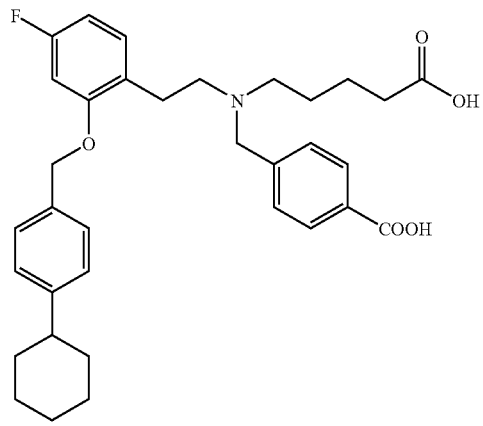

8 ml of a 2-molar solution of NaOH in water are added to a solution of 130 mg (0.22 mmol) of methyl 4-{[(2-{2-[(4-cyclohexylbenzyl)oxy]-4-fluorophenyl}ethyl)(5-methoxy-5-oxo-pentyl)amino]methyl}benzoate from Ex. V in 5 ml of THF, and the mixture is stirred at 60° C. for 15 hours. After cooling, the mixture is diluted with water and extracted with ether. The aqueous phase is adjusted to pH 4 to 5 using 1-molar hydrochloric acid. This results in the precipitation of the product, which is filtered off, washed with water and dried. This gives 92 mg (0.16 mmol, 74% yield) of a white solid.

Melting point: >250° C. $R_f$ (ethyl acetate/methanol 7:3): 0.20. $^1$H-NMR (300 MHz, DMSO-$d_6$, δ/ppm): 12.31 (2H, broad), 7.83 (2H, d), 7.32 (2H, d), 7.27 (2H, d), 7.18 (2H, d), 7.12 (1H, dd), 6.90 (1H, dd), 6.66 (1H, dt), 4.98 (2H, s), 3.59 (2H, s), 2.72–2.65 (2H, m), 2.59–2.51 (2H, m), 2.48 (1H, m, partially obscured by DMSO), 2.47–2.68 (2H, m), 2.10 (2H, t), 1.80–1.67 (5H, m), 1.44–1.19 (9H, m). MS (ESI): 562 (M+H$^+$).

The following compounds were obtained in an analogous manner:

| Ex. | Formula | $^1$H-NMR spectrum: δ[ppm] (DMSO-$d_6$) |
|---|---|---|
| 2 (from 2-hydroxy-5-fluorobenzaldehyde) | | 12.39 (2H, broad), 7.83(2H, d), 7.33–7.15 (6H, m), 7.02–6.95 (3H, m), 4.96(2H, s), 3.60 (2H, s), 2.78–2.69 (2H, m), 2.63–2.57 (2H, m), 2.48(1H, m, partially obscured by DMSO), 2.45–2.38 (2H, m), 2.16–2.07 (2H, m), 1.80–1.67(5H, m), 1.46–1.21(9H,m). (200MHz) |
| 3 (from 2-hydroxy-5-chlorobenzaldehyde and 4-(4-trifluoromethylphenyl)benzyl chloride) | | 12.33(2H, broad), 7.90–7.78 (6H, m), 7.71(2H, d), 7.47 (2H, d), 7.32(2H, d), 7.20 (2H, dd), 7.06–7.01(1H, m), 5.10(2H, s), 3.62(2H, s), 2.80–2.71(2H, m), 2.67–2.58 (2H, m), 2.46–2.39(2H, m), 2.15–2.05(2H, m), 1.44–1.37 (4H, m). (200 MHz) |

| Ex. | Formula | $^1$H-NMR spectrum: δ[ppm] (DMSO-$d_6$) |
|---|---|---|
| 4 (from 2-hydroxy-5-chlorobenzaldehyde and 4-(4-trifluoromethylphenyl)benzyl chloride) | | 12.37(2H, broad), 7.82(2H, d), 7.58(4H, d), 7.39(2H, d), 7.32(2H, d), 7.23–7.18(2H, m), 7.06–7.00(3H, m), 5.07 (2H, s), 3.80(3H, s), 3.61 (2H, s), 2.78–2.70(2H, m), 2.64–2.57(2H, m), 2.46–2.39 (2H, m), 2.16–2.07(2H, m), 1.44–1.37(4H, m). (200 MHz) |
| 5 (from 2-hydroxy-5-chlorobenzaldehyde) | | 7.81(2H, d), 7.30–7.22(4H, m), 7.21–7.16(4H, m), 7.02 (2H, d), 4.97(2H, s), 3.57 (2H, s), 2.71(2H, dd), 2.57 (2H, dd), 2.5(1H, obscured by DMSO), 2.40(2H, dd narrow), 2.10(2H, dd narrow), 1.80–1.63(5H, m), 1.42–1.19(9H, m). (300 MHz) |
| 6 (from 2-hydroxy-5-chlorobenzaldehyde and 4-(4-chlorophenyl)benzyl chloride) | | 12.33(2H, broad), 7.82(2H, d), 7.67(2H, d), 7.64(2H, d), 7.51(2H, d), 7.43(2H, d), 7.31(2H, d), 7.22–7.20(2H, m), 7.05–7.02(1H, m), 5.08 (2H, s), 3.61(2H, s), 2.76 (2H, dd), 2.60(2H, dd), 2.42 (2H, pseudo-t), 2.10(2H, pseudo-t), 1.43–1.37(4H, m). (300 MHz) |

-continued

| Ex. | Formula | ¹H-NMR spectrum: δ[ppm] (DMSO-d₆) |
|---|---|---|
| 7 (from 2-hydroxy-5-chlorobenzaldehyde and 4-(4-fluorophenyl)benzyl chloride) | | 12.29(2H, broad), 7.82(2H, d), 7.70–7.66(2H, m), 7.62 (2H, d), 7.42(2H, d), 7.31–7.27(4H, m), 7.21–7.19(2H, m), 7.03(1H, d), 5.07(2H, s), 3.61(2H, s), 2.74(2H, dd), 2.60(2H, dd), 2.42(2H, pseudo-t), 2.09(2H, pseudo t), 1.42–1.36(4H, m). (300 MHz) |
| 8 (from 2-hydroxy-5-chlorobenzaldehyde and 4-(4-cyanophenyl)benzyl chloride) | | 7.93–7.88(4H, m), 7.81(2H, d), 7.72(2H, d), 7.47(2H, d), 7.31(2H, d), 7.22–7.18(2H, m), 7.03–7.00(1H, m), 5.09 (2H, s), 3.61(2H, s), 2.73 (2H, dd), 2.61(2H, dd), 2.42 (2H, pseudo-t), 2.09(2H, pseudo-t), 1.43–1.37(4H, m). (200 MHz) |
| 9 (from 2-hydroxy-5-chlorobenzaldehyde and 4-(4-methoxyphenyl)-2-chlorobenzyl chloride) | | 12.36(2H, broad), 7.79(2H, d), 7.72(1H, d narrow), 7.63 (2H, d), 7.57–7.50(2H, m), 7.30–7.21(4H, m), 7.09–7.00 (3H, m), 5.09(2H, s), 3.81 (3H, s), 3.57(2H, s), 2.72 (2H, dd), 2.61(2H, dd), 2.38 (2H, pseudo-t), 2.07(2H, psuedo-t), 1.37(4H). (200 MHz) |

Ex. 10

4-{[(4-carboxybutyl)(2-{2-[(4-cyclohexylbenzyl)oxy]-4-fluorophenyl}ethyl)amino]methyl}benzoic acid hydrochloride

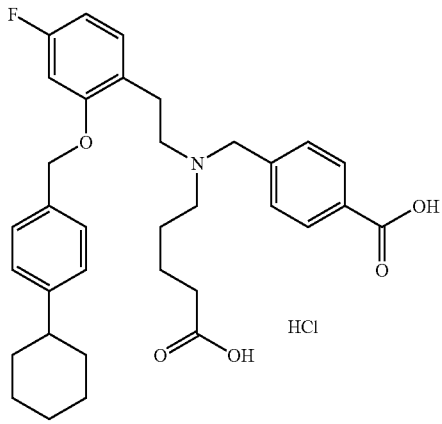

0.5 ml (2 mmol) of a 4-molar solution of HCl in dioxane is added to a solution of 220 mg (0.43 mmol) of 4-{[(4-carboxybutyl)(2-{2-[(4-cyclohexylbenzyl)oxy]-4-fluorophenyl}ethyl)amino]methyl}benzoic acid from Ex. 1 in 0.2 ml of dioxane, and the mixture is stirred at 60° C. for 1 h. The mixture is then concentrated by evaporation and the resulting colorless oil is triturated repeatedly with diethyl ether. The resulting crystals are filtered and dried.

Melting point: >250° C. $^1$H-NMR δ[ppm] DMSO-$d_6$:12.60 (2H, broad), 10.44 (1H, s broad), 7.97 (2H, d), 7.69 (2H, d), 7.32 (2H, d), 7.27–7.19 (3H, m), 7.01 (1H, dd), 6.74 (1H, dt), 5.04 (2H, s), 4.38 (2H, broad), 3.15–2.92 (6H, m), 2.46 (1H, m, partially obscured by DMSO), 2.14 (2H, t), 1.78–1.61 (6H, m), 1.46–1.21 (8H, m). (300 MHz)

The following compound was obtained in an analogous manner:

What is claimed is:

1. A compound of the general formula (I)

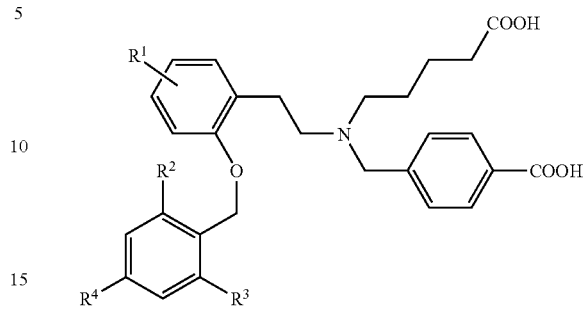

wherein
- $R^1$ is located in the meta- or para-position to the ethylamino radical and represents halogen;
- $R^2$ represents H or halogen;
- $R^3$ represents H or halogen;
- $R^4$ represents $C_{3-8}$-cycloalkyl or phenyl, where the phenyl radical may additionally carry a substituent from the group consisting of halogen, CN, OMe, $CF_3$;
  with the proviso that $R^4$ does not represent phenyl which carries a substituent $CF_3$ or OMe in the para-position to the point of attachment if, simultaneously, $R^1$ is in the meta-position to the ethylamino radical and represents F and $R^2$ and $R^3$ each represent H;
- or a pharmaceutically acceptable salt or stereoisomer thereof.

2. The compound as claimed in claim 1, characterized in that
- $R^1$ is located in the meta- or para-position to the ethylamino radical and represents F, Cl or Br;
- $R^2$ represents H or F or Cl;
- $R^3$ represents H;

| Ex. | Formula | $^1$H-NMR spectrum: δ[ppm] (DMSO-$d_6$) |
|---|---|---|
| 11 (from 2) | | 13.00(1H, broad), 12.32(1H, broad), 10.43(1H, s broad), 7.98(2H, d), 7.69(2H, d), 7.31(2H, d), 7.20–7.07(5H, m), 5.02(2H, s), 4.39(2H, broad), 3.18–2.97(6H, m), 2.44(1H, m, partially obscured by DMSO), 2.17 (2H, dd), 1.79–1.61(6H, m), 1.43–1.22(8H, m). (300MHz) |

R$^4$ represents cyclohexyl or phenyl, where the phenyl radical may additionally carry a substituent from the group consisting of F, Cl, Br, CN, OMe, CF$_3$;

with the proviso that R$^4$ does not represent phenyl which carries a substituent CF$_3$ or OMe in the para-position to the point of attachment if, simultaneously, R$^1$ is in the meta-position to the ethylamino radical and represents F and R$^2$ and R$^3$ each represent H;

or a pharmaceutically acceptable salt or stereoisomer thereof.

3. The compound as claimed in claim 1, characterized in that

R$^1$ is located in the meta-position to the ethylamino radical and represents Cl;

R$^2$ represents H or Cl;

R$^3$ represents H;

R$^4$ represents cyclohexyl or phenyl, where the phenyl radical may additionally carry a substituent from the group consisting of F, Cl, CN, OMe, CF$_3$;

or a pharmaceutically acceptable salt or stereoisomer thereof.

4. The compound as claimed in claim 1, characterized in that

R$^1$ is located in the para-position to the ethylamino radical and represents Cl or F;

R$^2$ represents H or Cl;

R$^3$ represents H;

R$^4$ represents cyclohexyl or phenyl, where the phenyl radical may additionally carry a substituent from the group consisting of F, Cl, CN, OMe, CF$_3$;

or a pharmaceutically acceptable salt or stereoisomer thereof.

5. A process for preparing compounds of the general formula (I), characterized in that compounds of the formula (II)

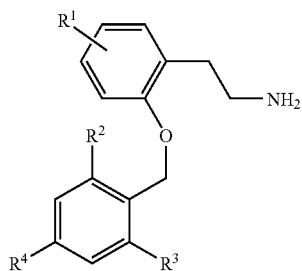

(II)

in which

R$^1$, R$^2$, R$^3$ and R$^4$ are as defined in claim 1, is reacted with a C$_{1-6}$-alkyl 4-formylbenzoate in an organic solvent with heating and with simultaneous or subsequent addition of a reducing agent to give compounds of the formula (III)

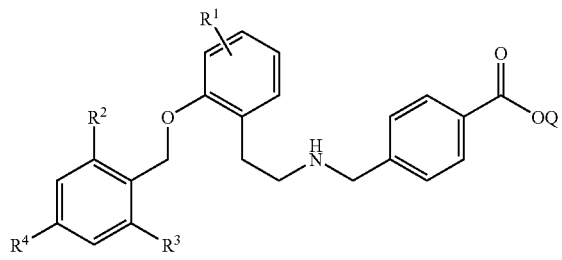

(III)

wherein

R$^1$, R$^2$, R$^3$ and R$^4$ are as defined above and Q represents a C$_{1-6}$-alkyl radical, then reacted with a C$_{1-6}$-alkyl ω-halovalerate in an organic solvent in the presence of a base with heating to give compounds of the formula (IV)

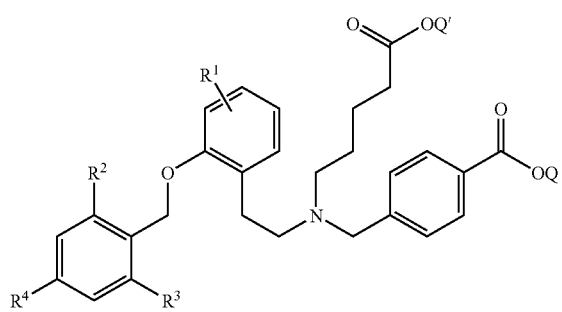

(IV)

wherein

R$^1$, R$^2$, R$^3$ and R$^4$ and Q are as defined above and Q' represents a C$_{1-6}$-alkyl radical, and the compounds of the formula (IV) is then hydrolyzed under alkaline conditions to give the compounds of the formula (I).

6. A pharmaceutical composition comprising a compound of claim 1 and a phramceutically acceptable carrier.

7. A method for treating angina pectoris or ischemias comprising administering to a subject in need thereof an effective amount of a compound of claim 1.

8. A method for treating hypertension, or arteriosclerosis comprising administering to a subject in need thereof an effective amount of a compound of claim 1.

9. A method for treating fibrosis of the liver comprising administering to a subject in need thereof an effective amount of a compound of claim 1.

* * * * *